United States Patent [19]

Shoji et al.

[11] Patent Number: 5,280,111

[45] Date of Patent: Jan. 18, 1994

[54] SULFATED TOCOPHERYL OLIGOSACCHARIDES AND ANTIVIRAL AGENTS INCLUDING THE SAME AS ACTIVE INGREDIENTS

[75] Inventors: Tadao Shoji; Naoya Ikushima; Kaname Katsuraya, all of Sakura; Nahoko Takahashi, Chiba; Fusayo Kobayashi, Sakura; Toshiyuki Uryu, Tokyo; Takashi Yoshida, Tokyo; Naoki Yamamoto, Tokyo; Hideki Nakashima, Tokyo, all of Japan

[73] Assignee: Dainippon Ink and Chemicals, Inc., Tokyo, Japan

[21] Appl. No.: 856,710

[22] Filed: Mar. 24, 1992

[30] Foreign Application Priority Data

Mar. 26, 1991 [JP] Japan .................. 3-61764
Mar. 26, 1991 [JP] Japan .................. 3-61765
Dec. 2, 1991 [JP] Japan .................. 3-317864
Dec. 9, 1991 [JP] Japan .................. 3-324532
Feb. 25, 1992 [JP] Japan .................. 4-37824

[51] Int. Cl.$^5$ .............. C07H 15/20; C07H 13/02; C07H 11/00; C07H 17/04; A61K 31/72
[52] U.S. Cl. .................. 536/4.1; 536/18.1; 536/123.1; 536/123.12; 536/123.13
[58] Field of Search .......... 536/4.1, 18.1, 123, 536/123.1, 123.12, 123.13; 514/25, 885

[56] References Cited

U.S. PATENT DOCUMENTS

| | | | |
|---|---|---|---|
| 4,457,918 | 7/1984 | Holick | 536/4.1 |
| 4,617,292 | 10/1986 | Satoh et al. | 536/4.1 |
| 4,868,206 | 8/1987 | Katsuragi et al. | 536/4.1 |
| 4,885,361 | 12/1989 | Wessel | 536/54 |
| 4,992,533 | 2/1991 | Kobayashi et al. | 536/4.1 |

FOREIGN PATENT DOCUMENTS

| | | |
|---|---|---|
| 0169716 | 1/1986 | . |
| 60-56994 | 4/1985 | Japan . |
| 61-30594 | 2/1986 | Japan . |
| 62-215529 | 9/1987 | Japan . |
| 1-103601 | 4/1989 | Japan . |

OTHER PUBLICATIONS

Advances in Carbohydrate Chemistry, 20, 183-218 (1965).
Advances in carbohydrate Chemistry, 25, 407&470-473 (1970).
Hideki Nakashima, et al., Jpn. J. Cancer Res. (Gann) 78, 1164-1168, Nov. 1987.
Patent Abstracts of Japan, unexamined application, C field, vol., No. 270, Jun. 12, 1990, The Patent Office Japanese Government p. 47 C 727 *Kokai-no 2-79 992*.
Biochemical Pharmacology, vol. 37, No. 15, 1988, Oxford, O. Yoshida et al "Sulfation of the Immunomodulating Polysaccharid Lentinan: A Novel Strategy for Antivirals to Human Immunodeficiency Virus (HIV)" pp. 2887-2891 *Totality*.

Primary Examiner—Ronald W. Griffin
Attorney, Agent, or Firm—Armstrong, Westerman, Hattori, McLeland & Naughton

[57] ABSTRACT

The present invention relates to novel tocopheryl oligosaccharides, acylated tocopheryl oligosaccharides, sulfated tocopheryl oligosaccharides, and antiviral agents including the sulfated tocopheryl oligosaccharides as active ingredients. In the tocopheryl oligosaccharide, the hydrogen atom of the hydroxy group at the 1-position in the terminal sugar moiety of an oligosaccharide which consists of 3~20 of identical or different repeating monosaccharide units selected from the group consisting of glucose, galactose, mannose, talose, idose, altrose, allose, glucose, xylose, arabinose, rhamnose, fucose, and fructose, which are glycoside-linked, is substituted by a tocopherol group. In the acylated tocopheryl oligosaccharides, each of any hydroxy group of the sugar moiety, other than the hydroxy group at the 1-position in the terminal sugar moiety of the oligosaccharide described above, is protected by an acyl group. The antiviral agents including the sulfated tocopheryl oligosaccharides or the biologically acceptable salt of the same as active ingredients have low toxicities and exhibit improved antiviral action, especially against the Human Immunodeficiency Virus.

12 Claims, No Drawings

SULFATED TOCOPHERYL OLIGOSACCHARIDES AND ANTIVIRAL AGENTS INCLUDING THE SAME AS ACTIVE INGREDIENTS

FIELD OF THE INVENTION

The present invention pertains to novel tocopheryl oligosaccharides, acylated tocopheryl oligosaccharides, sulfated tocopheryl oligosaccharides, antiviral agents including the sulfated tocopheryl oligosaccharides as active ingredients, and pharmaceutical compositions including the sulfated tocopheryl oligosaccharides as active ingredients. The antiviral agents according to the present invention have low toxicities and exhibit improved antiviral actions in particular on Human Immunodeficiency Virus (HIV).

BACKGROUND OF THE INVENTION

A tocopheryl glycoside as a water-soluble Vitamin E has been reported in U.S. Pat. No. 4,457,918, but which describes neither the concrete compounds including the oligosaccharides having three or more sugar residues, nor the antiviral actions thereof.

Japanese Patent Application First Publication Nos. 60-56994 and 61-30594 describe one- or two-sugar linked tocopheryl glycoside derivatives. However, in these documents, there is no description of the compounds including the oligosaccharides having three or more sugar residues and the tocopheryl glycosides in which lactoses are linked to galactoses, nor are the possibilities for using the same as starting materials of the compounds exhibiting the antiviral actions disclosed.

With regard to sugar sulfates, heretofore, monosaccharide sulfates and polysaccharide sulfates have been known and there are numerous reports related to the sulfates, e.g., Advances in Carbohydrate Chemistry, 20, 183, and Advances in Carbohydrate Chemistry, 25, 407.

Recently, a number of reports have been published wherein the polysaccharide sulfates are useful as the medical agents for Acquired Immune Deficiency Syndrome (AIDS). The reports include, for example, Japanese Patent Application First Publication No. 62-215529, Hideki Nakashima, et al., Jpn. J. Cancer Res. (Gann) 78, 1164 (1987); Osamu Yoshida, et al., Biochemical Pharmacology, 37, 2887–2891 (1988); Japanese Patent Application First Publication No. 1-103601; among others.

However, these polysaccharide sulfates have several disadvantages: they have antigenic properties and a strong tendency to act as anticoagulants, and are difficult to administer due to their poor absorption In vivo because of the molecular weights thereof being in excess of 10,000.

In addition, since 3'-azido-3'-deoxythymidine (AZT) (which is a nucleic acid derivative, and which has come to be broadly employed as an anti-AIDS agent) exhibits strong side effects, development of a novel chemical agent having low toxicity is desired.

SUMMARY OF THE INVENTION

It is an object of the present invention to provide novel and low toxicity compounds, having improved absorption in vivo, improved antiviral action, and in particular an anti-AIDS action.

As a result of various studies carried out by the inventors, according to the present invention, there are provided novel tocopheryl oligosaccharides, acylated or sulfated tocopheryl oligosaccharides, and antiviral agents including the sulfated tocopheryl oligosaccharides as active ingredients.

According to one aspect of the present invention, there is provided a tocopheryl oligosaccharide wherein the hydrogen atom of the hydroxy group at the 1-position in the terminal sugar moiety of an oligosaccharide which consists of identical or different repeating monosaccharide units which are glycoside-linked, is substituted by a tocopheryl group.

According to another aspect of the present invention, there is provided a tocopheryl oligosaccharide wherein the hydrogen atom of the hydroxy group at the 1-position in the terminal sugar moiety of an oligosaccharide which consists of identical or different repeating monosaccharide units which are glycoside-linked, is substituted by a tocopheryl group; and wherein each of any hydroxy group of the sugar moiety (other than the hydroxy group at the 1-position in the terminal sugar moiety of the oligosaccharide) is protected by an acyl group.

According to still another aspect of the present invention, there is provided a sulfated tocopheryl oligosaccharide or the biologically acceptable salt of the same, wherein the hydrogen atom of the hydroxy group at the 1-position in the terminal sugar moiety of an oligosaccharide which consists of identical or different repeating monosaccharide units which are glycoside-linked, is substituted by a tocopheryl group; and wherein each of any hydroxy group of the sugar moiety (other than the hydroxy group at the 1-position in the terminal sugar moiety of the oligosaccharide) is sulfated in the range of 10% and 100.0%.

According to a further aspect of the present invention, there is provided an antiviral agent including a sulfated tocopheryl oligosaccharide or the biologically acceptable salt of the same as an active ingredient.

According to a further aspect of the present invention, there is provided a pharmaceutical composition including a sulfated tocopheryl oligosaccharide or the biologically acceptable salt of the same as an active ingredient.

The above objects, effects, features, and advantages of the present invention will become more apparent from the following description of preferred examples thereof.

DETAILED DESCRIPTION OF THE INVENTION

The present invention provides novel tocopheryl oligosaccharides, acylated tocopheryl oligosaccharides, and sulfated tocopheryl oligosaccharides, and antiviral agents including the sulfated tocopheryl oligosaccharides as active agents.

The sugars of the oligosaccharide moieties in the tocopheryl oligosaccharides, or the acylated or sulfated tocopheryl oligosaccharides according to the present invention include the identical or different repeating monosaccharides selected from the group consisting of glucose, galactose, mannose, talose, idose, altrose, allose, glucose, xylose, arabinose, rhamnose, fucose, and frucose.

In view of antiviral activities, the number of the identical or different repeating monosaccharides of the above-described oligosaccharide moieties is chosen depending on the kinds of the sugars employed. In general, the number of the monosaccharides is preferably in the range of 3 to 20 in consideration of in vivo suitability and anticoagulant properties, which exhibited in the case of the sulfated polysaccharides.

With regard to the glycoside-linkages between the monosaccharides of the oligosaccharide moieties in the tocopheryl oligosaccharides, or the acylated or sulfated tocopheryl oligosaccharides used in an antiviral agent according to the present invention, any of (1→2)-, (1→3)-, (1→4)-, and (1→6)-glycoside-linkages is acceptable. In the case where an α(1→4)-glycoside-linked oligosaccharide glycoside (which tends to be decomposed in vivo) is used as an antiviral agent, the glycoside readily loses activity due to metabolism within the living body. In order to maintain the activity of the α(1→4)-glycoside-linked oligosaccharide glycoside, a greater daily dosage of this glycoside is required than that of the other glycosides which are more difficult to decompose.

Therefore, as the oligosaccharide moiety in the sulfated tocopheryl oligosaccharide according to the present invention, the β-configurational oligosaccharide, which has a relatively small decomposition property, is preferable in comparison with the α-configurational derivative. On the other hand, the regio-chemistry of the oligosaccharide moiety should be preferably in the (1→3)- or (1 6)-linkage, compared with (1→4)-linkage.

For example, the oligosaccharide moiety described above includes preferably a β(1→3)oligoglucose (an oligosaccharide in which glucose moieties are β(1→3)-glycoside-linked), in other words, an oligosaccharide obtained by decomposition of a polysaccharide such as curdlan, laminarane, or the like; an oligosaccharide in which galactose is β(1→4)-glycoside-linked at the 4-position in the galactose moiety of lactose and in which galactose moieties are β(1→4)-glycoside-linked in succession to the newly formed terminal galactose moieties; or the like.

An α(1→4)-glycoside-linked oligosaccharide such as oligomaltose is also acceptable as the oligosaccharide moiety. In addition, it is possible to use a mannose-type oligosaccharide, an β(1→6)oligoglucose, a β(1→6)oligoglucose, a xylan-type, schizophyllan-type, lentinan-type, or galactan-type oligosaccharide, or the like, as the oligosaccharide moiety.

For example, the usable oligosaccharide moiety includes malto-oligosaccharide, laminari-oligosaccharide, schizophyllan type of oligosaccharide, a purlane-type oligosaccharide, a lactose-containing galactose-type oligosaccharide, a xylan-type oligosaccharide, or the like. A part of the hydroxy groups of the oligosaccharide may be substituted with any substituted or unsubstituted amino groups.

The oligosaccharide moieties can be chemically produced by means of an acid decomposition reaction of a β(1→3) polysaccharide such as curdlan using acetic anhydride, acetic acid, sulfuric acid, and the like. In order to isolate the desired oligosaccharides, the reaction product may be purified by column chromatography on activated carbon or silica gel, as necessary. Decomposition of (1→3)polysaccharides using enzymes is acceptable, instead of the above-described chemical decomposition.

The lactose-type oligosaccharides wherein galactoses or galactose-type oligosaccharides are linked to the lactose moieties can be synthesized by means of a fermentation synthesis method using microorganisms belonging to the genus Cryptcoccus; this method is disclosed in Japanese Patent Application First Publication No. 2-79992 (1990).

The sugar having a lactose skeleton at the terminal thereof includes, for example, 4,6-di-O-(β-galactosyl)-glucose, β-D-galactosyl(1→4)lactose, β-D-galactosyl(1→6)lactose, β-D-galactosyl(1→4)galactosyl-β(1→4)lactose, β-D-galactosyl(1→4)galactosyl-β(1→4)galactosyl-β(1→4)lactose, or the like. In addition, the sugars produced by means of the fermentation method can be chemically elongated using the sugar residue extension reaction.

In the tocopheryl oligosaccharides, or the acylated or sulfated tocopheryl oligosaccharides according to the present invention, the hydroxy groups at the 6-position in the tocopherols are ether-linked to the hydroxy groups of the oligosaccharides.

All types of the tocopherol are acceptable in the present invention, such as dl-, d-, or l-derivative, and α-,β-,γ-,δ-,ε-,ζ-, or η-derivatives.

The compounds of the present invention can be produced according to various methods. For example, the compounds of the present invention are synthesized by glycosylation of the acetylated oligosaccharides obtained by acetylating the hydroxy groups of the oligosaccharides using the Keonigs-Knnor method or the like. The procedures of this method are as follows.

An oligosaccharide having the appropriate sugar residues is acetylated using acetic anhydride and sodium acetate according to a conventional method to obtain an acetylated oligosaccharide. Subsequently, the acetylated oligosaccharide is dissolved in an appropriate aprotic solvent: for example, a halogenated hydrocarbon such as methylene chloride, an aromatic hydrocarbon such as toluene, nitrobenzene, or the like. The reaction solution of the acetylated oligosaccharide is reacted with a tocopherol in the presence of an acid catalyst, for example: a protic acid such as para-toluenesulfonic acid; a Lewis acid such as zinc chloride, tin chloride, boron trifluoride ether complex; a triflate of a sulfonic acid such as trimethylsilyl triflate, or the like.

The reaction of the acetylated oligosaccharide with a tocopherol is generally carried out for 0.5 hours to 10 hours at $-30°$ C. $\sim 100°$ C. In the case where a protic acid or a Lewis acid is employed, the reaction temperature is preferably set to a relatively high temperature, i.e., ranging from room temperature to 100° C. In the case where trifluoromethyl triflate is used as the acid catalyst, the reaction temperature is preferably set to a relatively low temperature, i.e. ranging from 0° C. to $-30°$ C.

The mole ratio of a tocopherol based on the acetylated oligosaccharide is usually in the range of 1.0 to 2.0, and the excess tocopherol is preferably used. The acid catalyst is employed in the range of 0.1 to 2.0 mole equivalent per 1.0 mole equivalent of the acetylated oligosaccharide, and preferably in the range of 0.5 to 1.0 mole equivalent per 1.0 mole equivalent of the acetylated oligosaccharide.

The crude tocopheryl glycoside peracetate obtained in the above-described reaction can be purified according to a conventional method such as column chromatography on silica gel, recrystallization, or the like.

In the case where the desired glycoside is synthesized using an oligosaccharide peracetate and a Lewis acid at approximately room temperature, the β-derivative is obtained as a major product, while the yield of the α-derivative is small. On the other hand, in the case where a heteropolyacid is used as the acid catalyst instead of the Lewis acid in the glycoside formation, the yield of the α-derivative is greater than in the case of the Lewis acid. As a raw material of the antiviral agent according to the present invention, either the α-derivatives or β-derivatives are acceptable.

Acyl groups which are protective groups of the hydroxyl groups in the tocopheryl oligosaccharide can be easily deprotected by a deacetylation reaction using sodium methoxide or ammonium gas in methanol, according to a conventional method, thus the desired tocopheryl oligosaccharide can be obtained.

The hydroxy group of the obtained tocopheryl oligosaccharide is sulfated according to a conventional method to obtain a sulfated tocopheryl oligosaccharide. The sulfated tocopheryl oligosaccharide may be obtained in the form of a biologically acceptable salt such as sodium salt, potassium salt, magnesium salt, or the like.

Hydroxy groups of the tocopheryl oligosaccharide can be sulfated, using a sulfating agents such as sulfur trioxide pyridine complex, sulfur trioxide triethylamine complex, chlorosulfonic acid, piperidinesulfonic acid, or the like, for example in an aprotic polar solvent, in accordance with a conventional method.

The sulfation reaction is carried out using the sulfating agents in the appropriate amount corresponding to the desired sulfate index based on the hydroxy groups of the sugar, for 0.5 hours to 48 hours at a temperature ranging from room temperature to 100° C., and preferably ranging from room temperature to 85° C. In order to carry out complete sulfation, hydroxy groups of the sugar should be fully reacted with an excess of the sulfating agent.

After completion of the sulfation reaction, the reaction mixture is poured into water. Subsequently, the hydrogen ion concentration of the mixture is adjusted in the range of 7 to 10, and then the mixture is concentrated under reduced pressure. The steps of pouring water into the residue and then concentrating the mixture, are repeated two or three times. From the obtained residue, each of the sulfated tocopheryl glycoside and the inorganic salt of the same can be isolated using a separation system such as a "MAIKUROA-SHIRAIZA®" (a desalting device, produced by ASAHIKASEI INDUSTRIES Co., Ltd.), a gel filtration, a dialysis membrane, or the like. The solution from which the inorganic salt is removed is poured into a solvent such as acetone, an alcohol, or the like to obtain the desired sulfated tocopheryl oligosaccharide by a reprecipitation method.

The sulfation degree is indicated by a sulfation index. The sulfation index (%) is equal to the number of sulfated hydroxy groups divided by the number of all hydroxy groups which have the potential to be sulfated, multiplied by 100.

For example, in a tocopheryl oligosaccharide having five hexanoses, if all hydroxy groups are sulfated, the sulfation index (%) is 100% according to the following equation:

$$16/16 \times 100 \ (\%) = 100\%$$

If only two hydroxy groups of the 16 hydroxy groups are sulfated, the sulfation index (%) is 12.5% as follows:

$$2/16 \times 100 \ (\%) = 12.5\%$$

In order to obtain the desired sulfation index, the amount of the sulfating agent is adjusted based on the total number of hydroxy groups of a tocopheryl oligosaccharide.

The toxicity of the oligosaccharide is inversely affected by the sulfation index of the same. The antiviral activity of the oligosaccharide is proportionally affected by the sulfation index. Therefore, 10% or more of the all hydroxy groups of the glycoside should be sulfated, and it is preferable that the sulfation index be as high as possible.

The biologically acceptable salts are those derived from such biologically acceptable cations as sodium ion, potassium ion, magnesium ion, and the like.

Examples of acceptable sulfated tocopheryl oligosaccharides according to the present invention are listed below. In the list, the "sulfated compounds" have a sulfation index of 10% or more.

1) Sulfated tocopheryl oligosaccharides having the identical repeating monosaccharides Sulfated dl-α-tocopheryl β-D-glucopyranosyl(1→3)-β-D-glucopyranosyl(1→3)-β-D-glucopyranoside;

Sulfated dl-α-tocopheryl β-D glucopyranosyl(1→3)-β -D-glucopyranosyl(1→3)-β-D-glucopyranosyl(1→3)-β-D-glucopyranoside;

Sulfated dl-β-tocopheryl β-D-glucopyranosyl(1→3)-β-D-glucopyranosyl(1→3)-β-D-glucopyranosyl(1→3)-β-D-glucopyranosyl(1→3)-β-D-glucopyranoside;

Sulfated dl-α-tocopheryl β-D-glucopyranosyl(1→3)-β-D-glucopyranosyl(1→3)-β-D-glucopyranosyl(1→3)-β-D-glucopyranosyl(1→3)-β-D-glucopyranosyl(1→3)-β-D-glucopyranoside;

Sulfated dl-β-tocopheryl β-D-glucopyranosyl(1→3)-{β-D-glucopyranosyl(1→3)}$_n$-β-D-glucopyranoside;

Sulfated dl-α-tocopheryl β-D-glucopyranosyl(1→4)-β-D-glucopyranosyl(1→4)-β-D-glucopyranoside;

Sulfated dl-α-tocopheryl β-D-glucopyranosyl(1→4)-β-D-glucopyranosyl(1→4)-β-D-glucopyranosyl(1→4)-β-D-glucopyranoside;

Sulfated dl-α-tocopheryl β-D-glucopyranosyl(1→4)-β-D-glucopyranosyl(1→4)-β-D-glucopyranosyl(1→4)-β-D-glucopyranosyl(1→4)-β-D-glucopyranoside;

Sulfated dl-α-tocopheryl β-D-glucopyranosyl(1→4)-β-D-glucopyranosyl(1→4)-β-D-glucopyranosyl(1→4)-β-D-glucopyranosyl(1→4)-β-D-glucopyranosyl(1→4)-β-D-glucopyranoside;

Sulfated dl-α-tocopheryl β-D-glucopyranosyl(1→4)-{β-D-glucopyranosyl(1→4)}$_n$-β-D-glucopyranoside;

Sulfated dl-α-tocopheryl α-D-glucopyranosyl(1→4)-α-D-glucopyranosyl(1→4)-β-D-glucopyranoside;

Sulfated dl-α-tocopheryl β-D-glucopyranosyl(1→4)-α-D-glucopyranosyl(1→4)-α-D-glucopyranosyl(1→4)-β-D-glucopyranoside;

Sulfated dl-α-tocopheryl α-D-glucopyranosyl(1→4)-α-D-glucopyranosyl(1→4)-α-D-glucopyranosyl(1→4)-α-D-glucopyranosyl(1→4)-β-D-glucopyranoside;

Sulfated dl-α-tocopheryl β-D-glucopyranosyl(1→4)-α-D-glucopyranosyl(1→4)-α-D-glucopyranosyl(1→4)-α-D-glucopyranosyl(1→4)-α-D-glucopyranosyl(1→4)-β-D-glucopyranoside;

Sulfated dl-α-tocopheryl α-D-glucopyranosyl(1→4)-{α-D-glucopyranosyl(1→4)}$_n$-β-D-glucopyranoside;

Sulfated dl-α-tocopheryl β-D-glucopyranosyl(1→6)-β-D-glucopyranosyl(1→6)-β-D-glucopyranoside;

Sulfated dl-α-tocopheryl β-D-glucopyranosyl(1→6)-β-D-glucopyranosyl(1→6)-β-D-glucopyranosyl(1→6)-β-D-glucopyranoside;

Sulfated dl-α-tocopheryl β-D-glucopyranosyl(1→6)-β-D-glucopyranosyl(1→6)-β-D-glucopyranosyl(1→6)-β-D-glucopyranosyl(1→6)-β-D-glucopyranoside;

Sulfated dl-α-tocopheryl β-D-glucopyranosyl(1→6)-β-D-glucopyranosyl(1→6)-β-D-glucopyranosyl(1→6)-β-D-glucopyranosyl(1→6)-β-D-glucopyranosyl(1→6)-β-D-glucopyranoside;

Sulfated dl-α-tocopheryl β-D-glucopyranosyl(1→6)-{β-D-glucopyranosyl(1→6)}$_n$-β-D-glucopyranoside;

Sulfated dl-α-tocopheryl α-D-glucopyranosyl(1→6)-α-D-glucopyranosyl(1→6)-β-D-glucopyranoside;

Sulfated dl-α-tocopheryl α-D-glucopyranosyl(1→6)-α-D-glucopyranosyl(1→6)-α-D-glucopyranosyl(1→6)-β-D-glucopyranoside;

Sulfated dl-α-tocopheryl α-D-glucopyranosyl(1→6)-α-D-glucopyranosyl(1→6)-α-D-glucopyranosyl(1→6)-α-D-glucopyranosyl(1→6)-β-D-glucopyranoside;

Sulfated dl-α-tocopheryl α-D-glucopyranosyl(1→6)-α-D-glucopyranosyl(1→6)-α-D-glucopyranosyl(1→6)-α-D-glucopyranosyl(1→6)-α-D-glucopyranosyl(1→6)-β-D-glucopyranoside;

Sulfated dl-α-tocopheryl α-D-glucopyranosyl(1→6)-{α-D-glucopyranosyl(1→6)}$_n$-β-D-glucopyranoside;

Sulfated dl-α-tocopheryl β-D-galactopyranosyl(1→6)-β-D-galactopyranosyl(1→6)-β-D-galactopyranoside;

Sulfated dl-α-tocopheryl β-D-galactopyranosyl(1→6)-β-D-galactopyranosyl(1→6)-β-D-galactopyranosyl(1→6)-β-D-galactopyranoside;

Sulfated dl-α-tocopheryl β-D-galactopyranosyl(1→6)-β-D-galactopyranosyl(1→6)-β-D-galactopyranosyl(1→6)-β-D-galactopyranosyl(1→6)-β-D-galactopyranoside;

Sulfated dl-α-tocopheryl β-D-galactopyranosyl(1→6)-β-D-galactopyranosyl(1→6)-β-D-galactopyranosyl(1→6)-β-D-galactopyranosyl(1→6)-β-D-galactopyranosyl(1→6)-β-D-galactopyranoside;

Sulfated dl-α-tocopheryl β-D-galactopyranosyl(1→6)-{β-D-galactopyranosyl(1→6)}$_n$-β-D-galactopyranoside;

Sulfated dl-α-tocopheryl α-D-mannopyranosyl(1→2)-α-D-mannopyranosyl(1→2)-α-D-mannopyranoside;

Sulfated dl-α-tocopheryl α-D-mannopyranosyl(1→2)-α-D-mannopyranosyl(1→2)-α-D-mannopyranosyl(1→2)-α-D-mannopyranoside;

Sulfated dl-α-tocopheryl α-D-mannopyranosyl(1→2)-α-D-mannopyranosyl(1→2)-α-D-mannopyranosyl(1→2)-α-D-mannopyranoside;

Sulfated dl-α-tocopheryl β-D-mannopyranosyl(1→2)-α-D-mannopyranosyl(1→2)-α-D-mannopyranosyl(1→2)-α-D-mannopyranosyl(1→2)-α-D-mannopyranosyl(1→6)-α-D-mannopyranoside; and Sulfated dl-α-tocopheryl α-D-mannopyranosyl(1→2)-α-D-mannopyranosyl(1→2)}$_n$-α-D-mannoopyranoside.

In the compounds described above, "n" designates an integer in the range of 6 to 18.

Sulfated dl-α-tocopheryl α-D-glucopyranosyl(1→4)-α-D-glucopyranosyl(1→3)-β-D-glucopyranoside;

Sulfated dl-α-tocopheryl α-D-glucopyranosyl(1→3)-α-D-glucopyranosyl(1→4)-α-D-glucopyranosyl(1→3)-β-D-glucopyranoside;

Sulfated dl-α-tocopheryl α-D-glucopyranosyl(1→4)-α-D-glucopyranosyl(1→3)-α-D-glucopyranosyl(1→4)-α-D-glucopyransoyl(1→3)-β-D-glucopyranoside;

Sulfated dl-α-tocopheryl β-D-glucopyranosyl(1→3)-α-D-glucopyranosyl(1→4)-α-D-glucopyranosyl(1→3)-α-D-glucopyranosyl(1→4)-α-D-glucopyranosyl(1→3)-β-D-glucopyranoside; and Sulfated dl-α-tocopheryl α-D-glucopyranosyl(1→3)-{α-D-glucopyranosyl(1→4)-α-D-glucopyranosyl(1→3)}$_m$-β-D-glucopyranoside.

In the compounds described above, "m" designates an integer in the range of 3 to 9.

In addition, β-, γ-, δ-, ε-, ζ-, and η-tocopheryl derivatives as well as α-tocopheryl derivatives listed above are included in the present invention.

2) Sulfated tocopheryl oligosaccharides having different repeating monosaccharides Sulfated dl-α-tocopheryl β-D-galactopyranosyl(1→4)-β-D-galactopyranosyl(1→4)-β-D-glucopyranoside;

Sulfated dl-α-tocopheryl β-D galactopyranosyl(1→4)-β-D-galactopyranosyl(1→4)-β-D-galactopyranosyl(1→4)-β-D-glucopyranoside;

Sulfated dl-α-tocopheryl β-D-galactopyranosyl(1→4)-β-D-galactopyranosyl(1→4)-β-D-galactopyranosyl(1→4)-β-D-galactopyranosyl(1→4)-β-D-glucopyranoside;

Sulfated dl-α-tocopheryl β-D-galactopyranosyl(1→4)-β-D-galactopyranosyl(1→4)-β-D-galactopyranosyl(1→4)-β-D-galactopyranosyl(1→4)-β-D-galactopyranosyl(1→4)-β-D-glucopyranoside;

Sulfated dl-α-tocopheryl β-D-galactopyranosyl(1→4)-{β-D-galactopyranosyl(1→4)}$_n$-β-D-glucopyranoside;

Sulfated dl-α-tocopheryl β-D-galactopyranosyl(1→6)-β-D-galactopyranosyl(1→4)-β-D-glucopyranoside;

Sulfated dl-α-tocopheryl β-D-galactopyranosyl(1→6)-β-D-galactopyranosyl(1→6)-β-D-galactopyranosyl(1→4)-β-D-glucopyranoside;

Sulfated dl-α-tocopheryl β-D-galactopyranosyl(1→6)-β-D-galactopyranosyl(1→6)-β-D-galactopyranosyl(1→6)-β-D-galactopyranosyl(1→4)-β-D-glucopyranoside;

Sulfated dl-α-tocopheryl β-D-galactopyranosyl(1→6)-β-D-galactopyranosyl(1→6)-β-D-galactopyranosyl(1→6)-β-D-galactopyranosyl(1→6)'-β-D-galactopyranosl(1→4)-β-D-glucopyranoside; and Sulfated dl-α-tocopheryl β-D-galactopyranosyl(1→6)-{β-D-galactopyranosyl(1→6)}$_p$-β-D-galactopyranosyl(1→4)-β-D-glucopyranoside.

In the compounds described above, "p" designates an integer in the range of 3 to 17.

In addition β-, γ-, δ-, ε-, ζ-, and η-tocopheryl derivatives as well as α-tocopheryl derivatives listed above are included in the present invention.

Listings of the specific concrete derivatives of the tocopheryl oligosaccharides and the acylated tocopheryl oligosaccharides according to the present invention are omitted from the above list. The tocopheryl oligosaccharides correspond to the compounds in which the sulfated groups of the listed compounds are substituted with the hydroxy groups. The acylated tocopheryl oligosaccharides correspond to the compounds in which the hydroxy groups of the tocopheryl oligosaccharides are substituted with the acyloxy groups. Therefore, both the tocopheryl oligosaccharides and the acylated tocopheryl oligosaccharides are easily understandable from the listed compounds.

The antiviral agents according to the present invention exhibit antiviral activities against various viruses and are useful in treatment of either a disease that a pathogenic virus has generated or a conjugated disease of the same. The antiviral agents according to the present invention have in particular improved antiviral activities against the AIDS virus.

The mechanism of the antiviral activity of the compounds according to the present invention is not yet known. It may be conjectured that the compounds of the present invention have binding-inhibitory actions on the target cells of the virus. This is presumably due to the fact that the molecules of the compounds of the present invention are smaller, compared with polysaccharides, and have oleophilic groups such as tocopheryl groups, as well as hydrophilic groups such as hydroxy groups of sugars and the sulfuric groups. For these reasons, it may also be conjectured that the antiviral agents are easily able to approach the active portions of the virus.

In antiviral agents having the sulfated tocopheryl oligosaccharides of the present invention as active ingredients, the percentages of the active ingredients in the antiviral agents depend on the formulations. In general, 0.1%~100% of the active ingredients may be preferably included in the antiviral agents.

The antiviral agents using the active ingredients described above may be administered orally or parenterally in the pharmaceutical dosage forms such as tablets, capsules, granules, pills, liquids, injectable liquids, syrups, and the like.

The pharmaceutically acceptable excipients and additives known in the art may be used to prepare the above-described dosage forms of the pharmaceutical composition. Suitable excipients include water, a physiological saline, an alcohol, polyethylene glycol, glycerol ester, gelatin, carbohydrate magnesium stearate, talc, and the like. Suitable additives include antiseptics, antibacterial agents, lubricants, coating agents, wetting agents, emulsifiable concentrates, coloring agents, masking flavors, flavors, and the like.

In general, the antiviral agents according to the present invention are ordinarily administered several times in dosages ranging from 0.1 mg to 150 mg per kg of body weight per day, and more preferably in dosages ranging from 0.5 mg to 100 mg per kg of body weight per day, although variations will necessarily occur depending upon the weight and condition of the subject being treated and the particular route and the number of daily administrations chosen. The number of administrations is decided depending on the weight and condition of the subject being treated and the particular route of administration chosen. It is preferable to administer the antiviral agents of the present invention one to three times per day. Continuous intravenous drip injection of the antiviral agent is also acceptable.

The antiviral agents according to the present invention are effective for retroviruses, and in particular for the treatment and prevention of AIDS caused by the HIV retrovirus.

Furthermore, in the acute toxicity test performed for the sulfated tocopheryl oligosaccharide of the present invention, in which single doses were orally administered to groups of six mice, the results revealed that for each of the compounds of Examples 9 to 14 described below, at a dosage of 1.0 g/kg, all mice survived. The LD50 (lethal dose 50: the dose of substance which is fatal to 50% of the test animals) of the oral administration of each compound according to the present invention is 1 g/kg or more.

Examples

Hereinbelow, the preferred examples of the present invention will be explained. The examples are not intended in any way to limit the scope of the invention.

In the data of the proton nuclear magnetic resonance spectrum described in this specification, the chemical shift values (ppm), the integral values (the number of protons), the coupling constants (Hz), and the patterns are shown. With regard to signal patterns, a doublet is abbreviated as "d", a double doublet is abbreviated as "dd", a triplet is abbreviated as "t", a multiplet is abbreviated as "m", and a broad peak is abbreviated as "b".

Example 1

(Synthesis of acylated tocopheryl oligosaccharide)
Synthesis of dl-α-tocopheryl β-D-galactosyl-(1→4)-β-D-lactoside peracetate A solution of 30.8 g of β-D-galactosyl(1→4)-D-lactose peracetate and 19.82 g of dl-α-tocopherol dissolved in 160 ml of anhydrous methylene chloride was reacted with 5.8 ml of trimethylsilyl triflate for 22 hours at −11° C. in a stream of nitrogen gas. After completion of the reaction, 3.7 ml of triethylamine was added to the reaction mixture and stirred for 10 minutes. The stirred reaction mixture was subjected to the conventional after-treatment. The obtained crude product was purified by column chromatography on silica gel (eluate: hexane/ether=1/1 in volume), whereby the desired oily β-anomer derivative was obtained in the amount of 12.74 g.

Specific rotation $[\alpha]_D = -1.51°$
(c=1.05, chloroform, 30° C.)
Proton nuclear magnetic resonance spectrum (CDCl$_3$) (tetramethylsilane basis) ppm

| | | | |
|---|---|---|---|
| (1) the terminal galactose moiety: | | | |
| 1-position | 4.50 | d | 8 Hz |
| 2-position | 5.17 | dd | 8 Hz, 10 Hz |
| 3-position | 5.01 | dd | 10 Hz, 3.2 Hz |
| 4-position | 5.37 | dd | 3.2 Hz, ca. 1 Hz |
| 5-position | 3.69 | bt | 6 Hz |
| 6-position | ca. 4.1 | m | (2H) |
| (2) the intermediate galactose moiety: | | | |
| 1-position | 4.42 | d | 8 Hz |
| 2-position | 4.97 | dd | 8 Hz, 10 Hz |
| 3-position | 4.86 | dd | 10 Hz, 3.2 Hz |
| 4-position | ca. 4.12 | | |
| 5-position | 3.83 | bt | 6 Hz |
| 6a-position | 4.33 | dd | 4.2 Hz, 12 Hz |
| 6b-position | 4.16 | dd | 6.8 Hz, 12 Hz |
| (3) the glucose moiety: | | | |
| 1-position | 4.66 | d | 7.2 Hz |
| 2-position | 5.2~5.27 | | |
| 3-position | 5.2~5.27 | | |
| 4-position | ca. 3.87 | | |
| 5-position | 3.42 | m | |
| 6a-position | 4.39 | bdd | |
| 6b-position | ca. 4.1 | | |
| (4) the tocopheryl moiety and the acetyl moiety: | | | |
| 2.55 | t | 2H | J = 6.4 Hz |
| | the benzyl group | | |
| 1.98~2.17 | 39H | | |
| | the acetylmethyl moiety, and | | |
| | the tocopheryl aromatic methyl moiety | | |
| 0.8~1.9 | 38H | | |

Example 2

(Synthesis of tocopheryl oligosaccharide)
Synthesis of dl-α-tocopheryl β-D-galactosyl(1→4)-β-D-lactoside 55 ml of 0.1N sodium methoxide solution in methanol was added to a solution of 11.42 g of the compound obtained in Example 1 dissolved in 144 ml of methanol after 15 minutes in a stream of nitrogen gas. The mixture was stirred for 5 hours at room temperature. After removal of the insoluble matter from the mixture by filtration, 5 ml of Amberlite IR-120 ® (H+ type) was added to the filtrate and then the filtrate mixture was stirred for approximately 30 minutes. The filtrate without the resin was concentrated, whereby the desired product was obtained in the amount of 7.78 g.

Specific rotation $[\alpha]_D = +5.2°$
(c=0.52, methanol, 32° C.)

Infrared spectrum (main absorption value) (cm$^{-1}$)
3400, 2950, 1640, 1560, 1380, 1250, 1060

Proton nuclear magnetic resonance spectrum (CD$_3$OD) (tetramethylsilane basis) ppm

| 4.39 | d | 1H | J = 7.2 Hz |
|---|---|---|---|
| | the anomeric proton | | |
| 4.46 | d | 1H | J = 7.2 Hz |
| | the anomeric proton | | |
| 4.53 | d | 1H | J = 7.2 Hz |
| | the anomeric proton | | |
| 3.2~4.1 | the other protons of the sugar ring | | |
| 2.58 | m | 2H | |
| | the benzyl moiety | | |
| 2.22, 2.18, 2.04 | 3H × 3 | | |
| | the methyl protons in the aromatic ring | | |
| 1.77 | m | 2H | |
| 0.85~1.65 | 36H | | |

Example 3

(Synthesis of acylated tocopheryl oligosaccharide)
Synthesis of dl-α-tocopheryl β-D-glucosyl(1→3)-{β-D-glucosyl(1→3)}$_3$-βD-glucoside peracetate One g of β-D-glucosyl(1→3)-{β-D-glucosyl(1→3)}$_3$-βD-glucoside peracetate and 0.56 g of dl-α-tocopherol were dissolved in 10 ml of anhydrous methylene chloride. Molecular sieves 4A were added to the solution and then cooled to −8° C. under an argon atmosphere. The cooled mixture was reacted with 0.125 ml of trimethylsilyl triflate for 4 hours under an argon atmosphere.

After completion of the reaction, 0.09 ml of trimethylamine was added to the reaction mixture and then stirred for 30 minutes. The reaction mixture was subjected to the conventional after-treatment. The obtained crude product was purified by column chromatography on silica gel (eluate: hexane/ethyl acetate=⅔ in volume), whereby 0.548 g of the desired β-anomer derivative was obtained in the form of white solid.

| Specific rotation | $[\alpha]_D = -43.9°$ |
|---|---|
| | (c = 1.0, chloroform, 28° C.) |
| Mass spectrum | (FD method) (main peak, m/z) |
| | 1935 (M$^+$ + Na) |

Proton nuclear magnetic resonance spectrum (CDCl$_3$) (tetramethylsilane basis) ppm

| 0.83~1.90 | 38H |
|---|---|
| | the alkane protons of the topopheryl moiety |
| 1.97~2.22 | 57H |
| | the acetylmethyl moiety, and the tocopheryl aromatic methyl moiety |
| 2.55 | 2H |
| | the benzyl position |
| 3.4~5.06 | 35H |
| | the protons of sugar residues |

The characteristic peaks:

| 4.39, 4.41, 4.51, 4.52, 4.58 | J = 8 Hz (each) |
|---|---|
| | each 1-positional proton |
| 5.12 | t   J = 9.2 Hz |
| | the 3-positional proton of the terminal sugar located at the opposite side of the tocopheryl moiety |
| 5.30 | dd   J = 8.0 Hz, 9.6 Hz |
| | the 2-positional proton of the sugar having the tocopheryl group |

Example 4

(Synthesis of tocopheryl oligosaccharide)
Synthesis of dl-α-tocopheryl β-D-glucosyl(1→3)-{β-D-glucosyl(1→3)}$_3$-βD-glucoside 12.5 ml of 0.1N sodium methoxide solution in methanol was added to the solution of 0.50 g of dl-α-tocopheryl β-D-glucosyl(1→3)-{β-D-glucosyl(1→3)}$_3$-βD-glucoside peracetate obtained in Example 3 dissolved in 50 ml of methanol and then stirred for 28 hours at room temperature. The precipitated white solid was isolated by filtration under reduced pressure, subsequently washed with methanol, and then dried, whereby the desired product was obtained in the amount of 0.291 g.

| Specific rotation | $[\alpha]_D = -4.2°$ |
|---|---|
| | (c = 0.56, dimethylsulfoxide, 26° C.) |
| Infrared spectrum | (main absorption value) (cm$^{-1}$) |
| | 3400, 2940, 1640, 1560, 1380, 1250, 1180, 1080, 1040 |
| Mass spectrum | (FD method) (main peak, m/z) |
| | 1263 (M$^+$ + Na) |

Proton nuclear magnetic resonance spectrum ((CD$_3$)$_2$SO) (tetramethylsilane basis) ppm

| 0.81~1.60 | 36H |
|---|---|
| | the alkane protons of the topopheryl moiety |
| 1.73 | 2H |
| 2.08 | 2H |
| | the benzyl position |
| 1.98, 2.14, 2.16 | 3H > 3 |
| | the aromatic methyl protons |
| 3.0~3.8 | 30H |
| | the protons of sugar rings (2-position ~ 6-position) |
| 4.3~5.5 | 21H |
| | the protons of the alcoholic hydroxy group, and the anomeric protons |

Example 5

(Synthesis of acylated tocopheryl oligosaccharide)
Synthesis of dl-α-tocopheryl β-D-glucosyl(1→3)-{β-D-glucosyl(1→3)}$_7$-βD-glucoside peracetate 0.50 g of β-D-glucosyl(1→3)-{β-D-glucosyl(1→3)}$_7$-βD-glucoside peracetate was reacted with 0.30 g of dl-α-tocopheryl and then subjected to the after-treatment according to the procedures described in Example 3, whereby 0.22 g of the desired product was obtained in the form of white solid.

| Specific rotation | $[\alpha]_D = -46.2°$ |
|---|---|
| | (c = 0.20, chloroform, 28° C.) |
| Mass spectrum | (FD method) (main peak, m/z) |
| | 3087 (M$^+$ + Na) |

Proton nuclear magnetic resonance spectrum (CDCl$_3$) (tetramethylsilane basis) ppm

| 0.83~1.90 | 38H |
|---|---|

-continued

| | | |
|---|---|---|
| 1.97~2.22 | 93H | the alkane protons of the topopheryl moiety the acetylmethyl moiety, and the tocopheryl aromatic methyl moiety |
| 2.55 | 2H | the benzyl position |
| 3.4~5.06 | 63H | the protons of sugar residues |
| The characteristic peaks: | | |
| 4.39~4.59 | 1H × 9   J = 8 Hz (each) | 1-positional protons |
| 5.12 | 1H   t   J = 9.2 Hz | the 3-positional proton of the terminal sugar located at the opposite side of the tocopheryl moiety |
| 5.30 | 1H   dd   J = 8.0 Hz, 9.6 Hz | the 2-positional proton of the sugar having the tocopheryl moiety |

Example 6

(Synthesis of tocopheryl oligosaccharide)

Synthesis of dl-α-tocopheryl β-D-glucosyl(1→3)-{β-D-glucosyl(1→3)}₇-βD-glucoside Sixteen ml of 0.1N sodium methoxide solution in methanol was added to the solution of 0.10 g of dl-α-tocopheryl β-D-glucosyl(1→3)-{β-D-glucosyl(1→3)}₇-βD-glucoside peracetate obtained in Example 5 dissolved in 50 ml of methanol and then stirred for 28 hours at room temperature. The precipitated white solid was isolated by filtration under reduced pressure, washed with methanol, and then dried, whereby the desired product was obtained in the amount of 0.055 g.

| | |
|---|---|
| Specific rotation | $[\alpha]_D = -5.8°$ (c = 0.40, dimethylsulfoxide, 30° C.) |
| Infrared spectrum | (main absorption value) (cm⁻¹) 3400, 2940, 1640, 1560, 1380, 1250, 1180, 1080, 1040 |
| Mass spectrum | (FD method) (main peak, m/z) 1911 (M⁺ + Na) (M⁺ indicates the molecular ion peak of the desired product) |
| Proton nuclear magnetic resonance spectrum ((CD₃)₂SO) (tetramethylsilane basis) ppm | |
| 0.81~1.60 | 36H the alkane protons of the topopheryl moiety |
| 1.73 | 2H |
| 2.08 | 2H the benzyl position |
| 1.98, 2.14, 2.16 | 3H × 3 the aromatic methyl protons (2-position ~ 6-position) |
| 4.3~5.5 | 37H the protons of the alcoholic hydroxy group, and the anomeric protons |

Example 7

(Synthesis of acylated tocopheryl oligosaccharide)

Synthesis of dl-α-tocopheryl β-D-galactosyl(1→4)-{β-D-galactosyl(1→4)-D-lactoside peracetate A solution of 4.48 g of β-D-galactosyl(1→4)-{β-D-galactosyl(1→4)-D-lactose peracetate and 3.04 g of dl-α-tocopherol dissolved in 12 ml of anhydrous methylene chloride was reacted with 0.58 ml of trimethylsilyl triflate for 24 hours at −11° C. under an argon atmosphere. After completion of the reaction, 0.37 ml of triethylamine was added to the reaction mixture and then stirred for 30 minutes. The mixture was subjected to the conventional after-treatment. The obtained crude product was purified by column chromatography on silica gel (eluate: hexane/ethyl acetate=⅓ in volume), whereby 2.46 g of the desired β-anomer derivative was obtained in the form of oil.

| | | | | |
|---|---|---|---|---|
| Specific rotation | $[\alpha]_D = -0.78°$ | | | |
| | (c = 1.0, chloroform, 28° C.) | | | |
| Proton nuclear magnetic resonance spectrum (CDCl₃) (tetramethylsilane basis) ppm | | | | |
| (1) the terminal galactose moiety: | | | | |
| 1-position | 4.44 | 1H | d | 8 Hz |
| 2-position | 5.20 | 1H | dd | |
| 3-position | 5.00 | 1H | dd | 11 Hz, 3Hz |
| 4-position | 5.37 | 1H | dd | 3 Hz |
| 5-position | 3.85 | 1H | bt | |
| 6-position | 4.11 | 2H | m | |
| (2) the intermediate galactose moiety of the terminal (galactose moiety side: | | | | |
| 1-position | 4.37 | 1H | d | 8 Hz |
| 2-position | 4.94 | 1H | dd | 8 Hz, 10 Hz |
| 3-position | 4.84 | 1H | dd | 10 Hz, 3 Hz |
| 4-position | 4.11 | 1H | m | |
| 5-position | 3.68 | 1H | bt | |
| 6a-position | 4.18 | 1H | dd | 7 Hz, 12 Hz |
| 6b-position | 6.40 | 1H | dd | |
| (3) the intermediate galactose moiety of the glucose moiety side: | | | | |
| 1-position | 4.43 | 1H | d | 8 Hz |
| 2-position | 5.03 | 1H | dd | 8 Hz, 10 Hz |
| 3-position | 4.89 | 1H | dd | 10 Hz, 3 Hz |
| 4-position | 4.11 | 1H | m | |
| 5-position | 3.64 | 1H | bt | |
| 6a-position | 4.15 | 1H | dd | 7 Hz, 12 Hz |
| 6b-position | 4.33 | 1H | dd | 5 Hz, 12 Hz |
| (4) the glucose moiety: | | | | |
| 1-position | 4.66 | 1H | d | 8 Hz |
| 2-position | 5.25 | 1H | dd | 8 Hz, 10 Hz |
| 3-position | 5.20 | 1H | dd | 10 Hz, 8 Hz |
| 4-position | 3.84 | 1H | t | |
| 5-position | 3.42 | 1H | m | |
| 6a-position | 4.11 | 1H | m | |
| 6b-position | 4.38 | 1H | m | |
| (5) the tocopheryl moiety and the acetyl moiety | | | | |
| 2.55 | 2H | t | | |
| | the benzyl group | | | |
| 1.97~2.20 | 39H | | | |
| | the acetylmethyl moiety, and the tocopheryl aromatic methyl groups | | | |
| 0.8~1.9 | 38H | | | |
| | the alkyl groups | | | |

Example 8

(Synthesis of tocopheryl oligosaccharide)

Synthesis of dl-α-tocopheryl β-D-galactosyl(1→4)-β-D-galactosyl(1→4)-β-D-lactoside Sixteen ml of 0.1N sodium methoxide solution in methanol was added to a solution of 1.23 g of the compound obtained in Example 7 dissolved in 36 ml of methanol after 30 minutes under an argon atmosphere. The mixture was stirred for 7 hours at room temperature. An ion exchange resin, Amberlite IR-120® (H+ type) was added to the reaction mixture and then stirred for 15 minutes. The mixture from which the ion exchange resin was removed was concentrated, whereby the desired product was obtained in the amount of 0.78 g.

Specific rotation $[\alpha]_D = +17.3°$
(c=0.53, methanol, 30° C.)
Infrared spectrum (cm⁻¹) 3400, 2950, 1640, 1460, 1380, 1250, 1060
Proton nuclear magnetic resonance spectrum (CD₃OD) (tetramethylsilane basis) ppm

| | | | |
|---|---|---|---|
| 4.40 | d | 1H | J = 7.2 Hz |
| | the anomeric proton | | |
| 4.45 | d | 1H | J = 7.2 Hz |
| | the anomeric proton | | |
| 4.47 | d | 1H | J = 7.2 Hz |
| | the anomeric proton | | |
| 4.54 | d | 1H | J = 7.2 Hz |
| | the anomeric proton | | |
| 3.2~4.0 | the other protons of the sugar ring | | |
| 2.58 | m | 2H | |
| | the benzyl position | | |
| 2.22, 2.18, 2.04 | | 3H × 3 | |
| | the methyl protons in the aromatic ring | | |
| 1.78 | m | 2H | |
| 0.85~1.65 | | 36H | |

Example 9

(Synthesis of sulfated tocopheryl oligosaccharide)

Synthesis of sulfated dl-α-tocopheryl β-D-galactosyl(1→4)-β-D-lactoside 8.67 g of sulfur trioxide pyridine complex was added to a solution of 1.54 g of dl-α-tocopheryl β-D-galactosyl(1→4)-β-D-lactoside dissolved in 77 ml of pyridine at 84° C. under an argon atmosphere and then stirred for 1.5 hours at 86° C. 24 ml of ion exchange water was added to the reaction mixture and then stirred for an hour. Subsequently, the reaction solution was allowed to stand at room temperature.

40% of the reaction solution was subjected to the following treatment: 0.5N sodium hydroxide solution was added to the reaction solution so that the pH of the reaction solution was approximately 10. Subsequently, 75 ml of ion exchange water was added to the reaction solution. The desaltation of the reaction product was carried out using a "MAIKUROASHIRAIZA®" (a desalting device, produced by ASAHIKASEI INDUSTRIES Co., Ltd.). After concentration of the resulting solution, precipitation was achieved by adding acetone thereto. The obtained precipitate was washed with acetone and subsequently dried, whereby the desired product was obtained in the amount of 1.8 g. As a result of analysis, the sulfation index was 63.0%.

Specific rotation $[\alpha]_D = -2.2°$
(c=1.19, $H_2O$, 32° C.)
Infrared spectrum (cm$^{-1}$)
3500, 2920, 1250, 1120, 800, 610

Example 10

(Synthesis of sulfated tocopheryl oligosaccharide)

Synthesis of sulfated ester sodium salt of dl-α-tocopheryl β-D-glucosyl(1→3)-{β-D-glucosyl(1→3)}$_3$-β-D-glucoside (1)

0.5 g of sulfur trioxide pyridine complex was added to a solution of 0.12 g of dl-α-tocopheryl β-D-glucosyl(1→3)-{β-D-glucosyl(1→3)}$_3$-β-D-glucoside)-dissolved in 10 ml of anhydrous pyridine at 84° C. in a stream of argon gas and then stirred for 1.5 hours at 70° C. After the reaction mixture was cooled to room temperature, 10 ml of ion exchange water was added to the reaction mixture and then stirred for an hour. Subsequently, 0.5N sodium hydroxide solution was added to the mixture so that the pH of the mixture was approximately 10.

After the mixture was concentrated under reduced pressure at 40° C., 10 ml of ion exchange water was added to the concentrated mixture. The desaltation of the reaction product was carried out using a "MAIKUROASHIRAIZA®" (a desalting device, produced by ASAHIKASEI INDUSTRIES Co., Ltd.) for 16 hours. After concentration of the resulting solution, precipitation was achieved by adding acetone thereto. The obtained precipitate was washed with acetone and subsequently dried, whereby the desired product was obtained in the amount of 0.25 g. As a result of analysis, the sulfation index of the hydroxy groups was 70%.

Specific rotation $[\alpha]_D = -7.9°$
(c=1.0, $H_2O$, 32° C.)
Infrared spectrum (cm$^{-1}$)
3500, 2950, 1640, 1250, 1120, 810, 610

| Proton nuclear magnetic resonance spectrum ($D_2O$) ppm | |
|---|---|
| 0.8~1.9 | 38H |
| | the alkane protons of the topopheryl moiety |
| 2.15 | 2H |
| | the benzyl position |
| 2.24, 2.28, 2.31 | 3H × 3 |
| | the aromatic methyl protons |
| 3.7~5.5 | 35H |
| | the protons of sugar residues |

Example 11

(Synthesis of sulfated tocopheryl oligosaccharide)

Synthesis of sulfated ester sodium salt of dl-α-tocopheryl β-D-glucosyl(1→3)-{β-D-glucosyl(1→3)}$_3$-β-D-glucoside (2)

0.6 g of sulfur trioxide pyridine complex was added to a solution of 0.15 g of dl-α-tocopheryl β-D-glucosyl(1→3)-{β-D-glucosyl(1→3)}$_3$-β-D-glucoside dissolved in 11 ml of anhydrous pyridine at 84° C. in a stream of an argon gas and then stirred for 6 hours at 70° C., according to the procedures described in Example 9. After the reaction mixture was cooled to room temperature, 10 ml of ion exchange water was added to the reaction mixture and then stirred for an hour. Subsequently, 0.5N sodium hydroxide solution was added to the mixture so that the pH of the mixture was approximately 10.

After the mixture was concentrated under reduced pressure at 40° C., 10 ml of ion exchange water was added to the concentrated mixture. The desaltation of the reaction product was carried out using a column chromatography on Sephadex®. After the fraction including the desired product was concentrated to half in volume, the precipitate was occurred by adding acetone thereto. The obtained precipitation was washed with acetone and subsequently dried, whereby the desired product was obtained in the amount of 0.28 g. As a result of analysis, the sulfation index of the hydroxy groups was 86%.

Specific rotation $[\alpha]_D = -7.8°$
(c=1.0, $H_2O$, 28° C.)
Infrared spectrum (cm$^{-1}$)
3500, 2950, 1640, 1240, 1120, 810, 610

Example 12

(Synthesis of sulfated tocopheryl oligosaccharide)

Synthesis of sulfated ester sodium salt of dl-α-tocopheryl β-D-glucosyl(1→3)-{β-D-glucosyl(1→3)}$_7$-β-D-glucoside 0.7 g of sulfur trioxide pyridine complex was added to a solution of 0.04 g of dl-α-tocopheryl β-D-glucosyl(1→3)-{ β-D-glucosyl(1→3)}$_7$-β-D-glucoside dissolved in 10 ml of anhydrous pyridine at 84° C. in a stream of an argon gas and then stirred for 7.5 hours at 70° C. After the reaction mixture was allowed to cool at room temperature, 10 ml of ion exchange water was added to the reaction mixture and then stirred for an hour. Subsequently, 0.5N sodium hydroxide solution was added to the mixture so that the pH of the mixture was approximately 10.

After the mixture was concentrated under reduced pressure at 40° C., 10 ml of the ion exchange water was added to the concentrated mixture. The desaltation of the reaction product was carried out using a column chromatography on Sephadex ®. After the fraction including the desired product was concentrated to half in volume, the precipitation was achieved by adding acetone thereto. The obtained precipitate was washed with acetone and subsequently dried, whereby the desired product was obtained in the amount of 0.052 g. As a result of analysis, the sulfation index of the hydroxy groups was 76%.

Specific rotation $[\alpha]_D = -6.5°$
(c=0.2, $H_2O$, 29° C.)
Infrared spectrum ($cm^{-1}$)
3500, 2950, 1640, 1250, 1120, 810, 610

| Proton nuclear magnetic resonance spectrum ($D_2O$) ppm | |
| --- | --- |
| 0.8~1.9 | 38H the alkane protons of the topopheryl moiety |
| 2.15 | 2H the benzyl position |
| 2.24, 2.28, 2.31 | 3H × 3 the aromatic methyl protons |
| 3.7~5.5 | 35H the protons of the sugar moieties |

Example 13

(Synthesis of sulfated tocopheryl oligosaccharide)
Synthesis of sulfated dl-α-tocopheryl β-D-galactosyl(1→4)-β-D-galactosyl(1→4)-β-D-lactoside 1.61 g of sulfur trioxide pyridine complex was added to a solution of 0.28 g of dl-α-tocopheryl β-D-galactosyl(1→4)-β-D-galactosyl(1→4)-β-D-lactoside dissolved in 11 ml of anhydrous pyridine at 51° C. in a stream of an argon gas and then stirred for one hour at 51° C. The mixture was stirred for 10 minutes at 81° C. and then stirred for 1.5 hours at 51° C. After the generated syrupy precipitate was isolated using pyridine by decantation, 4 ml of ion exchange water was added to the syrupy product, and then stirred for one hour at room temperature. Subsequently, 0.5N sodium hydroxide solution was added to the mixture so that the pH of the mixture was approximately 10.

After the mixture was concentrated under reduced pressure, 0.57 g of crude product was obtained. Seventeen ml of ion exchange water was added to the crude product. The desaltation of the product was carried out using a column chromatography on Sephadex ®. After the fraction including the desired product was concentrated to 1.5 ml, the precipitation was achieved by adding ethanol thereto. The obtained precipitate was filtrated and subsequently dried, whereby the desired product was obtained in the amount of 0.37 g. As a result of analysis, the sulfation index was 99.0%.

Specific rotation $[\alpha]_D = -2.1°$
(c=0.51, $H_2O$, 30° C.)
Infrared spectrum ($cm^{-1}$)
3500, 2950, 1640, 1250, 1020, 820, 590

Example 14

(Synthesis of sulfated tocopheryl oligosaccharide)
Synthesis of sulfated dl-α-tocopheryl β-D-galactosyl(1→4)-β-D-galactosyl(1→4)-β-D-lactoside 1.61 g of sulfur trioxide pyridine complex was added to a solution of 0.28 g of dl-α-tocopheryl β-D-galactosyl(1→4)-β-D-galactosyl(1→4)-β-D-lactoside dissolved in 11 ml of anhydrous pyridine in a stream of argon gas and then stirred for 1.5 hour at 84° C. The generated syrupy precipitate was subjected to a treatment similar to that as described in Example 9, whereby the desired product was obtained in the amount of 0.3 g. As a result of analysis, the sulfation index was 86.0%.

Specific rotation $[\alpha]_D = -1.2°$
(c=0.51, $H_2O$, 30° C.)
Infrared spectrum ($cm^{-1}$)
3500, 2950, 1640, 1250, 1020, 820, 590

Anti-HIV assay

Activity of the compound against HIV-1 replication was based on the inhibition of virus induced cytopathogenicity in MT-4 cells. MT-4 cells were suspended in culture medium at $2.5 \times 10^4$ cells/ml and infected with HIV-1 at a multiplicity of infection (MOI) of 0.01. 100 μl of cell suspension was brought into microtiter tray wells containing various concentrations of the test compounds.

After 5 days of incubation at 37° C. using a $CO_2$ incubator, the number of viable cells was determined by the MTT method.

The inhibitory effect on host cell viability (cytotoxicity) was also determined by the MTT method. All activities of the compounds are expressed as 50% inhibitory concentration, i.e., the concentration required to reduce the number of HIV-1-infected MT-4 cells or mock-infected MT-4 cells by 50%. These are expressed using $EC_{50}$ and $CC_{50}$. SI is expressed by the ratio of $CC_{50}/EC_{50}$. (Reference document: Pauwels, et al., J. Virol Methods, 20 (1988) 309~321).

According to this method, the anti-HIV assay was carried out using the compounds obtained in Examples 9 to 14. In addition, AZT (3'-azido-3'-deoxythymidine) known as an anti-AIDS agent was employed as a comparative example.

The results are shown in Table 1.

As will be apparent from the results shown in Table 1, the sulfated tocopheryl oligosaccharides according to the present invention exhibit superior effectiveness in SI.

TABLE 1

| Example No. | $CC_{50}$ (μg/ml) | $EC_{50}$ (μg/ml) | SI |
| --- | --- | --- | --- |
| 9 | 606 | 1.03 | 587 |
| 10 | >480 | 0.52 | >920 |
| 11 | >480 | 0.45 | >1000 |
| 12 | >480 | 0.44 | >1000 |
| 13 | 621 | 0.43 | 1444 |
| 14 | 656 | 0.57 | 1151 |
| AZT | 2.88 | 0.0013 | 2160 |

Hereinafter, formulation examples of the antiviral agents according to the present invention are shown.

Formulation Synthesis Example 1

| Compound obtained in Example 9 | 50 mg |

| | |
|---|---|
| Starch | 25 mg |
| Lactose | 116 mg |
| Talc | 6 mg |
| Magnesium stearate | 3 mg |
| Total | 200 mg |

The starch and lactose listed above were added to the ground compound obtained in Example 9. A starch paste was added to the mixture, and then the mixture was stirred to form granules. The granules were dried and graded. The talc and magnesium stearate listed above were added to the graded granules, and the mixture was subjected to formulation into tablet according to the conventional method, whereby a tablet weighing 200 mg was formed.

Formulation Synthesis Example 2

| | |
|---|---|
| Compound obtained in Example 10 | 50 mg |
| Starch | 30 mg |
| Lactose | 110 mg |
| Talc | 7 mg |
| Magnesium stearate | 3 mg |
| Total | 200 mg |

A tablet weighing of 200 mg was formed by repeating the same procedures described in Formulation Example 1, except that the compound obtained in Example 10 was used instead of the compound obtained in Example 9.

Formulation Synthesis Example 3

| | |
|---|---|
| Compound obtained in Example 11 | 50 mg |
| Starch | 30 mg |
| Lactose | 110 mg |
| Talc | 7 mg |
| Magnesium stearate | 3 mg |
| Total | 200 mg |

A tablet weighing 200 mg was formed by repeating the same procedures described in Formulation Example 1, except that the compound obtained in Example 11 was used instead of the compound obtained in Example 9.

Formulation Synthesis Example 4

| | |
|---|---|
| Compound obtained in Example 12 | 25 mg |
| Starch | 23 mg |
| Lactose | 50 mg |
| Magnesium stearate | 2 mg |
| Total | 100 mg |

The starch, lactose, and magnesium stearate listed above were added to the ground compound obtained in Example 12. The mixture was fully mixed and then packed into a capsule.

Formulation Synthesis Example 5

500 mg of the compound obtained in Example 13 was dissolved in a physiological saline sterilized in an autoclave, with the resulting volume of the solution being 10 ml. The solution was placed in a dry-sterilized ampule, whereby a liquid in the volume of 10 ml was formed.

Formulation Synthesis Example 6

500 mg of the compound obtained in Example 14 was dissolved in a physiological saline. The solution was subjected to a similar treatment as described in Formulation Example 4, whereby a liquid in the volume of 10 ml was formed.

Formulation Synthesis Example 7

A ground mixture of 500 mg of the compound obtained in Example 9, 1000 mg of mannitol, and 400 mg of disodium phosphate were placed in a dry-sterilized ampul, whereby an ampul in the volume of 10 ml was formed.

Formulation Synthesis Example 8

A ground mixture of 1.25 g of the compound obtained in Example 10 and 1 g of disodium phosphate were placed in a dry-sterilized vial, whereby a packed intraveneous drip vial was formed.

What is claimed is:

1. A sulfated tocopheryl oligosaccharide containing 3 to 20 monosaccharide units or a biologically acceptable salt of the same, wherein the hydrogen atom of the hydroxy group at the 1-position in the terminal sugar moiety of an oligosaccharide which consists of identical repeating monosaccharide units which are glycoside-linked, is substituted by a tocopherol group; and wherein each of any hydroxy group of the sugar moiety other than the hydroxy group at the 1-position in the terminal sugar moiety of the oligosaccharide is sulfated in the range of 10.0% to 100.0%.

2. A sulfated tocopheryl oligosaccharide or the biologically acceptable salt of the same as recited in claim 1, wherein the monosaccharide unit of the oligosaccharide is a monosaccharide selected from the group consisting of glucose, galactose, mannose, talose, idose, altrose, allose, xylose, arabinose, rhamnose, fucose, and fructose.

3. A sulfated tocopheryl oligosaccharide or the biologically acceptable salt of the same as recited in claim 1, wherein the tocopheryl group is the one selected from the group consisting of $\alpha$-, $\beta$-, $\gamma$-, $\delta$-, $\epsilon$-, $\zeta$-, and $\eta$-tocopheryl groups.

4. A sulfated tocopheryl oligosaccharide containing 3 to 20 monosaccharide units or a biologically acceptable salt of the same, wherein the hydrogen atom of the hydroxy group at the 1-position in the terminal sugar moiety of an oligosaccharide which consists of different repeating monosaccharide units which are glycoside-linked, is substituted by a tocopherol group; and wherein each of any hydroxy group of the sugar moiety other than the hydroxy group at the 1-position in the terminal sugar moiety of the oligosaccharide is sulfated in the range of 10.0% to 100.0%.

5. A sulfated tocopheryl oligosaccharide or the biologically acceptable salt of the same as recited in claim 4, wherein the monosaccharide unit of the oligosaccharide is a monosaccharide selected from the group consisting of glucose, galactose, mannose, talose, idose, altrose, allose, xylose, arabinose, rhamnose, fucose, and fructose.

6. A sulfated tocopheryl oligosaccharide or the biologically acceptable salt of the same as recited in claim 4, wherein the oligosaccharide moiety is a galactose oligosaccharide in which galactose is $\beta(1\rightarrow 4)$-glycoside-linked at the 4-position in the galactose moiety of lactose and in which galactose moieties are $\beta(1\rightarrow 4)$-glycoside-linked in succession to the newly formed terminal galactose moieties.

7. A pharmaceutical composition comprising a sulfated tocopheryl oligosaccharide or the biologically acceptable salt of the same as recited in claims 1 or 4 as an active ingredient and at least one ingredient selected from the group consisting of pharmaceutically acceptable excipient additive.

8. A pharmaceutical composition as recited in claim 7, which is an antiviral agent.

9. An antiviral agent as recited in claim 8, wherein the virus is a retrovirus.

10. An antiviral agent as recited in claim 9, wherein the virus is the HIV retrovirus. acceptable salt of the same as recited in of claim 1, as an active ingredient.

11. A pharmaceutical composition as recited in claim 7, the pharmaceutically acceptable excipient is at least one substance selected from the group consisting of water, a physiological saline, an alcohol, polyethylene glycol, glycerol ester, gelatin, carbohydrate magnesium stearate, and talc.

12. A pharmaceutical composition as recited in claim 7, the pharmaceutically acceptable additive is at least one substance selected from the group consisting of antiseptics, antibacterial agents, lubricants, coating agents, wetting agents, emulsifiable concentrates, coloring agents, masking flavors, and flavors.

* * * * *